United States Patent [19]
King

[11] Patent Number: 5,148,700
[45] Date of Patent: Sep. 22, 1992

[54] APPARATUS AND METHOD FOR LOCATING SEDIMENT IN A CONTAINER

[75] Inventor: Arthur V. King, Denton, Tex.

[73] Assignee: Entech Design, Inc., Denton, Tex.

[21] Appl. No.: 791,781

[22] Filed: Nov. 12, 1991

[51] Int. Cl.$^5$ ............................................. G01N 15/00
[52] U.S. Cl. ..................................... 73/61.41; 73/621; 367/104
[58] Field of Search ................. 73/621, 622, 623, 627, 73/619, 19.03, 61 R, 290 V; 367/104

[56] References Cited

U.S. PATENT DOCUMENTS

| | | | |
|---|---|---|---|
| 4,049,954 | 9/1977 | Da Costa Vieira et al. | 73/622 |
| 4,114,441 | 9/1978 | Magri | 73/290 V |
| 4,151,834 | 5/1979 | Sato et al. | 73/619 |
| 4,364,273 | 12/1982 | Redding | 73/614 |
| 4,782,702 | 11/1988 | Boone et al. | 73/629 |
| 4,815,048 | 3/1989 | Boucher et al. | 367/104 |

FOREIGN PATENT DOCUMENTS

| | | | |
|---|---|---|---|
| 0149042 | 11/1980 | Japan | 73/290 V |
| 2230608 | 10/1990 | United Kingdom | 73/290 V |

Primary Examiner—Michael Razavi
Assistant Examiner—Raymond Y. Mah
Attorney, Agent, or Firm—W. Kirk McCord

[57] ABSTRACT

Improved apparatus and method are provided for locating and mapping sediment in a container, which is at least partially filled with liquid. A sonar transducer is mounted with the container for emitting acoustic energy into the liquid and for receiving reflected acoustic energy. The sonar transducer is rotatable about mutually perpendicular first and second axes to provide a dual-axis capability. The transducer is controlled to emit discrete acoustic signals and receive reflected acoustic signals along discrete scanning axes at each rotational position in a predetermined sequence of rotational positions. The distance between the transducer and a corresponding point of reflection along each scanning axis is compared to a predetermined reference distance along the corresponding scanning axis. The reference distance represents the distance between the transducer and an inner surface of the container along the corresponding scanning axis. The points of reflection whose distances to the transducer are less than the respective reference distances are identified as sediment. The identified points are combined to form a three-dimensional representation of the sediment in the container. The three-dimensional representation is superimposed on a three-dimensional representation of the container, whereby one can continually monitor the quantity and location of the sediment in the container.

18 Claims, 12 Drawing Sheets

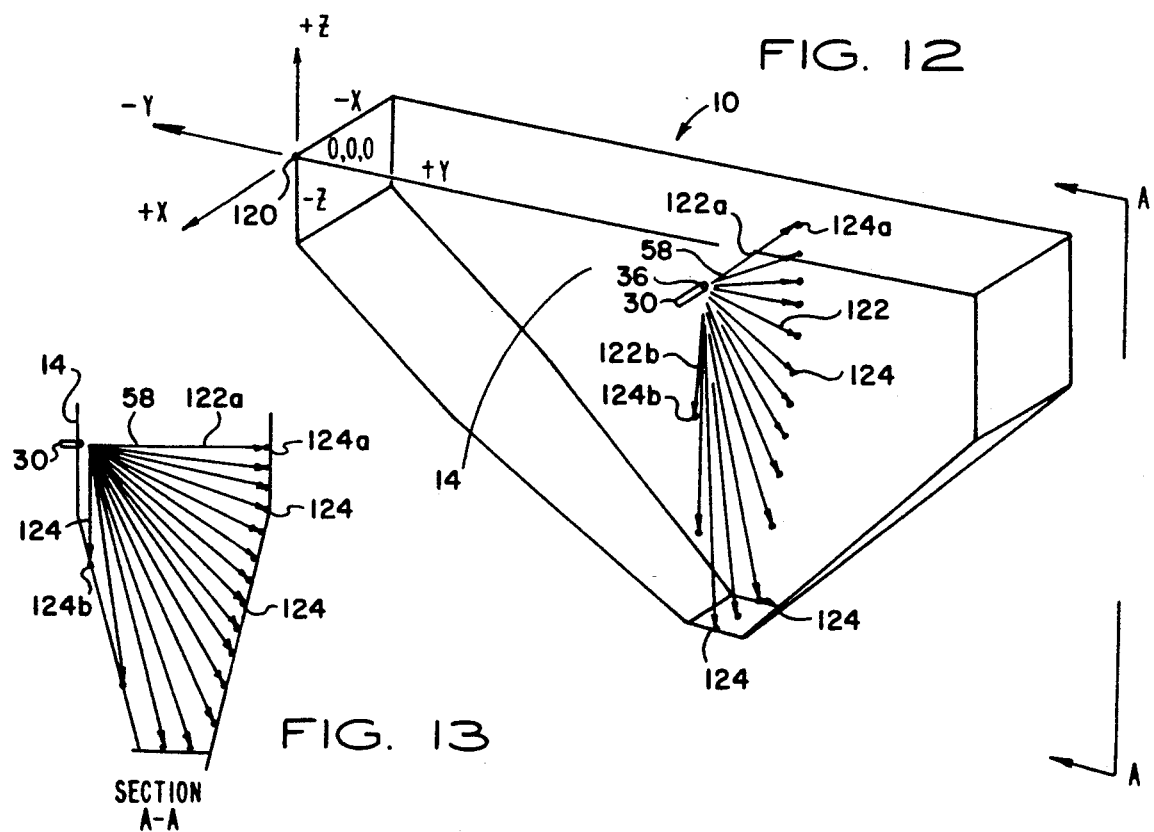

APPARATUS AND METHOD FOR LOCATING SEDIMENT IN A CONTAINER

FIELD OF INVENTION

This invention relates generally to containers for storing liquid and solid material and in particular to an apparatus and method for locating sediment in a container, which is at least partially filled with liquid.

BACKGROUND OF THE INVENTION

Utility companies in the Unites States burn coal and other fossil fuels in a combustion furnace, to generate steam in connection with the electrical power generation process. Coal is burned at a temperature of several thousand degrees Fahrenheit. The by-product of the combustion process is an ash material which may "clinker" or fuse together into large pieces. The ash pieces often collect and drip from the walls of the combustion furnace. When the ash is present in the furnace, the ash is at approximately the same temperature as the combustion gases in the furnace. The heavier pieces of ash, which fall to the bottom of the furnace, are referred to as "bottom ash".

Typically, a large container, which is sometimes referred to as a "hopper", is located beneath the furnace to collect the falling bottom ash. The hopper is constructed of structural steel and is lined on the inside with several inches of concrete refractory. The hopper is usually filled with a liquid, such as water, which is at a relatively high temperature. The refractory insulates the steel material from the hot water inside the hopper, to prevent burn injuries to personnel who come in contact with the steel material on the outside of the hopper. Furthermore, the water inside the hopper may become acidic or caustic. The refractory provides a corrosion protective layer between the steel material and the water. The refractory also provides an abrasion-resistant liner, to prevent the falling ash from contacting the steel material. The water inside the hopper cools the pieces of falling ash and facilitates break up of large pieces of ash. A constant supply of water is provided to the hopper.

The hopper is generally four-sided, with two vertical walls and two sloped walls. The bottom of the hopper includes a moveable door panel, to allow the ash sediment collected at the bottom of the hopper to be emptied. Hoppers may be constructed in various configurations, including single and multiple section hoppers.

Because of the massive size of the hopper, the extremely high temperatures of the furnace above the hopper and other conditions inside the hopper, such as the constant stream of ash pieces descending through the water in the hopper and the turbidity of the water inside the hopper, it is virtually impossible to visually inspect the interior of the hopper to determine how much ash sediment has been collected or to determine the location of the ash sediment in the hopper.

DESCRIPTION OF THE PRIOR ART

Prior art attempts to determine the amount and location of the ash sediment within a hopper have not been successful. According to prior practice, a plurality of contact probes are inserted into the hopper at selected intervals of depth for detecting the presence of solid material within the hopper. The probes are subjected to avalanches of ash material descending through the liquid in the hopper, which may damage the electrical components contained in the probes, thereby resulting in unreliable or incomplete data. Furthermore, a contact probe can only detect the presence of solid material at the particular location of the corresponding probe and cannot accurately determine the amount or location of ash sediment in the hopper.

Consequently, the current practice is to remove the ash sediment from the hopper on a periodic basis, irrespective of how much ash sediment is actually in the hopper. Therefore, the hopper may be emptied prematurely, when there is little or no ash sediment in the hopper, which results in unnecessary expenditure of electrical power. On the other hand, if the ash buildup in the hopper is excessive, the removal operation may not remove all of the ash, thereby resulting in a cumulative buildup of left-over ash sediment, which can cause forced plant outages. The aforementioned ash removal process costs a typical utility company many thousands of dollars a year.

DISCLOSURE OF THE INVENTION

In accordance with the present invention, an apparatus and method are provided for locating sediment in a container, which is at least partially filled with liquid. The apparatus includes a transducer mountable with the container for emitting acoustic energy into the liquid and for receiving reflected acoustic energy. The transducer is rotatable about first and second mutually perpendicular axes by respective first and second motive means. Control means is provided for controlling the first and second motive means to rotate the transducer about the respective first and second axes.

In operation, the control means controls the transducer to emit a discrete acoustic signal into the liquid and to receive a corresponding reflected acoustic signal at each rotational position of the transducer in a predetermined sequence of rotational positions. Each rotational position is definable by a first rotational coordinate with respect to the first axis and a second rotational coordinate with respect to the second axis. Processing means is responsive to the reflected acoustic signals for computing the respective distances between the transducer and respective points of reflection along respective scanning axes, corresponding to the respective rotational positions of the transducer. The computed distance along each scanning axis is compared with a predetermined reference distance representing the distance between the transducer and an inner surface of the container along the corresponding scanning axis, to identify each point of reflection whose computed distance is less than the corresponding reference distance. The identified points of reflection represent respective locations of the sediment in the container. The identified points are used to create a three-dimensional image of the sediment in the container.

In accordance with a unique feature of the invention, a three-dimensional image of the container in an empty condition is created and the three-dimensional image of the sediment is superimposed on the three-dimensional image of the empty container, whereby the quantity and location of the sediment in the container is visually determinable. In one embodiment, the three-dimensional image of the container is created by establishing a three-dimensional coordinate system and assigning respective three-dimensional coordinates to respective corner points of the container. The respective coordinates of the corner points are used to represent the container as a plurality of interconnected geometric planes. Each of the identified points of reflection is also assigned three-dimensional position coordinates so that the identified points of reflection representing respective locations of the sediment can be displayed with reference to the container.

In accordance with another feature of the invention, maximum and minimum distance parameters are established. The computed distance corresponding to each point of reflection is compared with the minimum and maximum distance parameters and those points whose computed distances are less than the minimum distance parameter or greater than the maximum distance parameter are eliminated from consideration.

In accordance with yet another feature of the invention, the computed distance corresponding to each point of reflection is compared with the computed distance corresponding to a previous point of reflection. The corresponding point of reflection is eliminated from consideration if the computed distance to the corresponding point of reflection is less than the computed distance to the previous point of reflection by more than a predetermined amount. The eliminated point is replaced with a replacement point of reflection by interpolating between the previous point of reflection and a next successive point of reflection.

In accordance with still another feature of the invention, mounting means is provided for mounting the transducer with the container. The mounting means includes a casing adapted for insertion into the container. The casing has an internal chamber for receiving the transducer and an opening communicating between the internal chamber and the liquid in the container when the casing is inserted into the container. A mounting flange projects from the casing into the chamber for mounting the transducer in a fixed position with respect to the casing such that a first portion of the transducer is able to penetrate through the opening into the liquid and a second portion of the transducer is carried in the chamber. In one embodiment, wherein the transducer has a housing and a collar member in concentric relation about the housing. The collar member is adapted to contact an inner surface of the casing adjacent the opening for substantially isolating the chamber from the liquid. In another embodiment, the casing further includes a locating flange projecting into the chamber adjacent the opening for engaging an outer surface of the collar member when the collar member is in contact with the inner surface of the casing. The locating flange cooperates with the inner surface of the casing to substantially isolate the chamber from the liquid. The locating flange is further adapted to limit movement of the first portion of the transducer in a direction perpendicular to a direction in which the first portion of the transducer is moveable through the opening into contact with the liquid in the hopper.

In accordance with yet another feature of the invention, fluid supply means is provided for supplying cooling fluid to the chamber and fluid discharge means is provided for discharging the cooling fluid from the chamber, whereby the transducer is cooled. In one embodiment, the apparatus further includes a conduit in fluid communication with the fluid discharge means for directing a flow of cooling fluid on the first portion of the transducer when the first portion of the transducer is in contact with the liquid. In another embodiment, deflector means is located in the container above the opening for deflecting solid material descending in the liquid away from the first portion of the transducer when the first portion of the transducer is in contact with the liquid.

In accordance with still another feature of the invention, the transducer includes acoustic signal generating means for generating the acoustic signals and acoustic signal receiving means for receiving the reflected acoustic signals, both of which are located in the first portion of the housing. The first portion of the housing isolates the acoustic signal generating means and the acoustic signal receiving means from the liquid in the container. Fluid material is located in the first portion of the housing for enhancing the transmission of acoustic energy between the acoustic signal generating means and the liquid and between the acoustic signal receiving means and the liquid. The fluid material is preferably electrically non-conductive to inhibit electrolytic action in the housing.

In accordance with the present invention, sediment in a container can be located and mapped to provide a three-dimensional representation of the sediment in the container. By superimposing the three-dimensional image of the sediment on a three-dimensional image of the container, one can readily determine the location and amount of the sediment. When the sediment reaches a predetermined level within the container, the sediment is preferably removed using conventional removal apparatus. The present invention reduces the expense associated with the sediment removal process by allowing an operator to continually monitor the buildup of sediment and to remove the sediment only when necessary.

DESCRIPTION OF THE FIGURES

FIG. 12 is a perspective view of a collection hopper, illustrating a sequence acoustic signals being transmitted by a sonar transducer along respective scanning axes;

FIG. 13 is a sectional view, taken along the line A—A of FIG. 12;

FIG. 14 is a perspective view of a collection hopper, illustrating respective points on corresponding inner surfaces of the hopper along the respective scanning axes;

DETAILED DESCRIPTION OF THE PREFERRED EMBODIMENT

Figure 1:
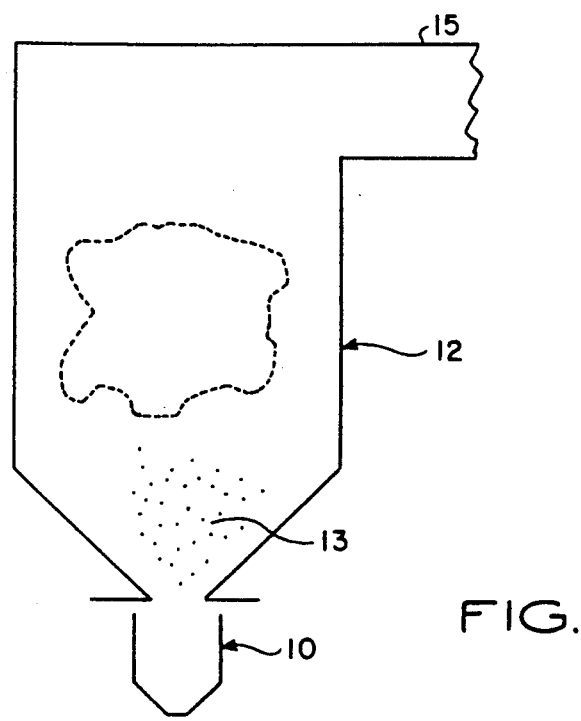
FIG. 1 is a sectional view of a combustion furnace and hopper for collecting solid material by-product of the combustion process.

In the description which follows, like parts are marked throughout the specification and drawings with the same respective reference numerals. The drawings are not necessarily to scale and in some instances proportions may have been exaggerated in order to more clearly depict certain features of the invention.

Referring now to FIG. 1, a steel hopper 10 is located beneath a combustion furnace 12 for collecting the solid byproduct of the combustion process, which typically includes pieces of ash, indicated by reference numeral 13. The gaseous products of combustion are typically discharged from furnace 12 through a stack 15.

Figure 2A:
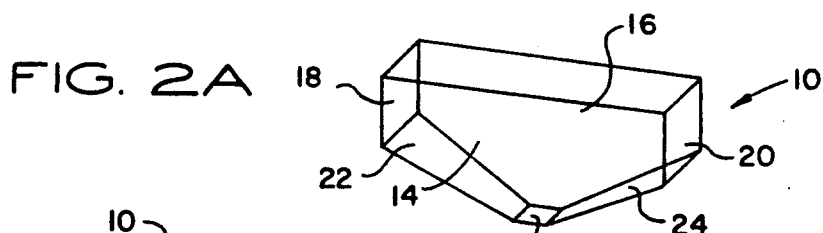
FIGS. 2A, 2B and 2C are respective perspective views of single unit, double unit and triple unit collection hopper sections, respectively.
Figure 2B:
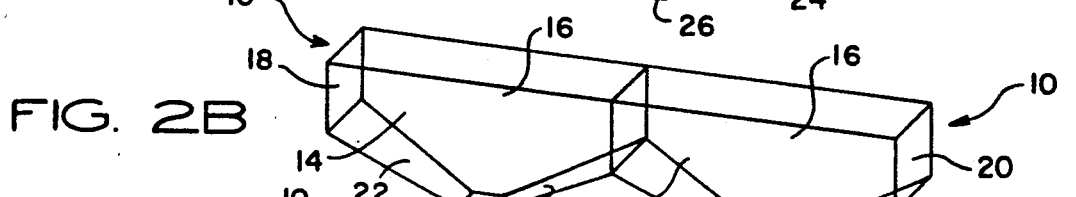
Figure 2C:
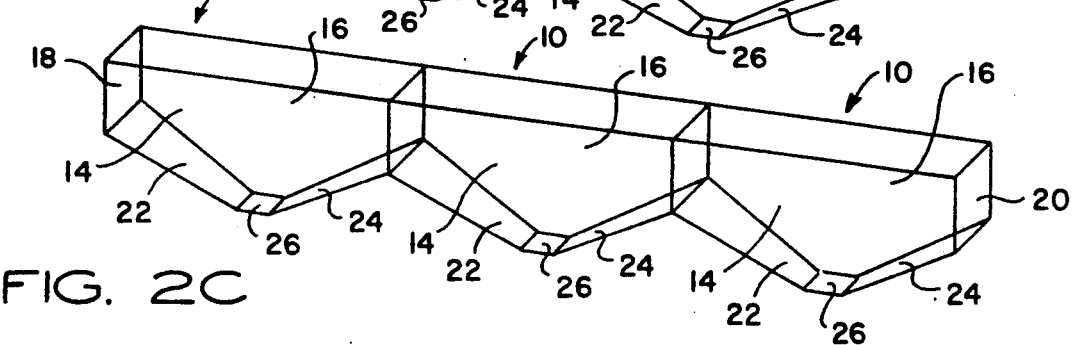

Referring now to FIG.'s 2A, 2B and 2C, hopper 10 is generally trapezoidal with front and back walls 14 and 16, respectively, opposed generally vertical side walls 18 and 20, respectively, and two sloped walls 22 and 24, respectively, which converge at the bottom of hopper 10. A moveable door panel is located adjacent a bottom portion 26 of hopper 10, to allow the sediment collected at the bottom of hopper 10 to be emptied. Hopper 10 is preferably filled with a liquid, such as water. A plurality of hoppers 10 may be arranged in one, two or three unit sections, as shown in FIGS. 2A, 2B and 2C, respectively.

Figure 3:
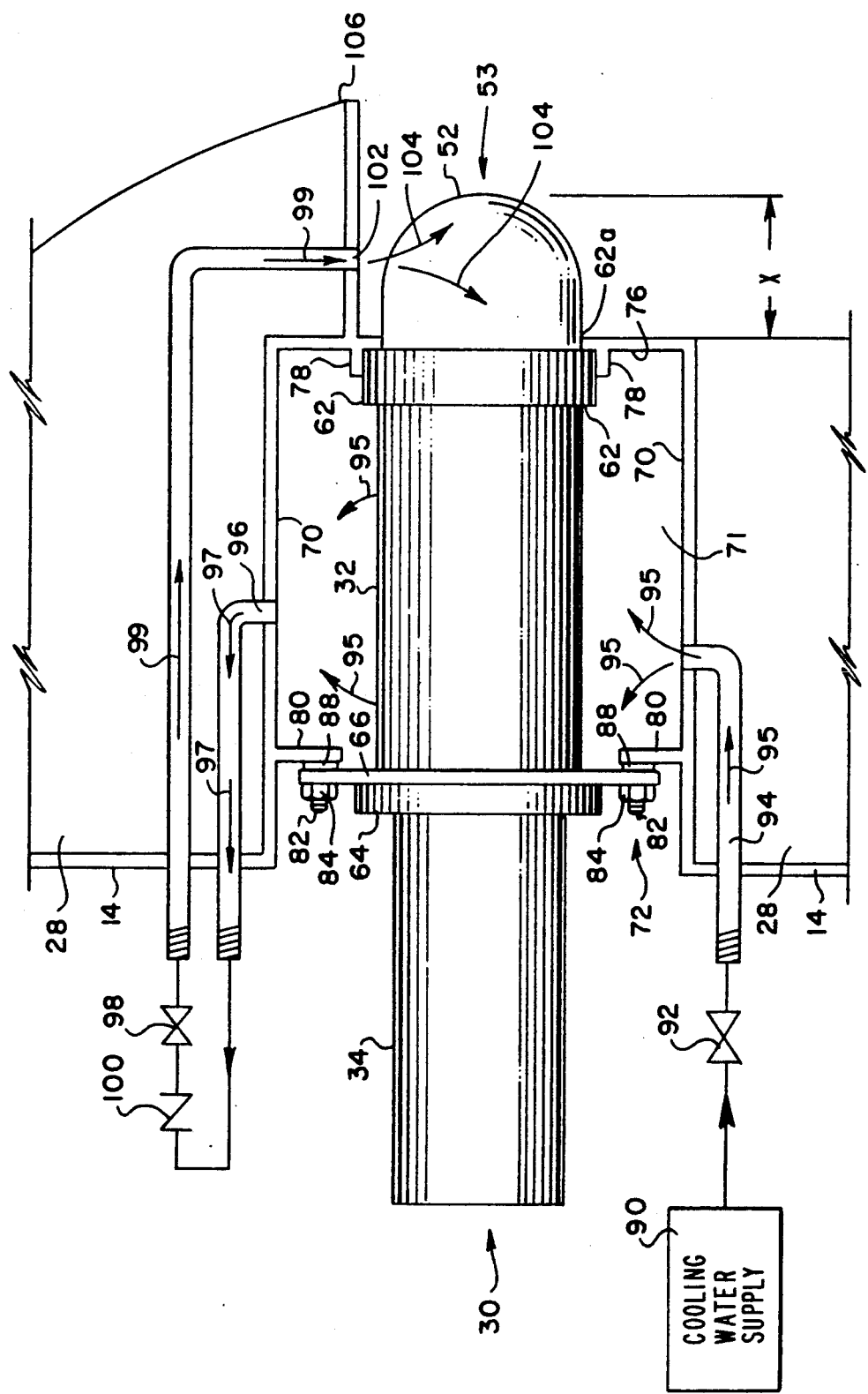
FIG. 3 is a detailed sectional view of a sonar transducer mounted in the wall of a collection hopper.
Figure 4:
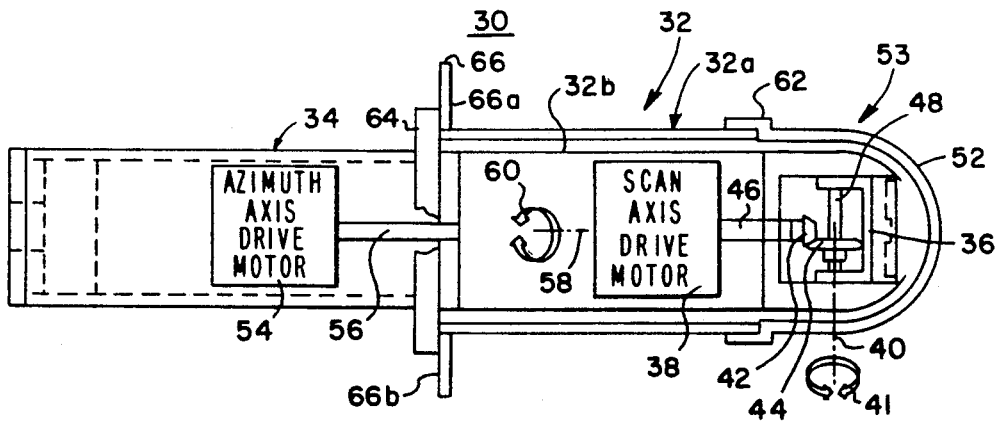
FIG. 4 is a sectional view of the sonar transducer of FIG. 3.

Referring now to FIG. 3, the interior steel surfaces of hopper 10 are lined with concrete refractory material 28, to insulate the steel material from the heat and corrosive effect of the liquid inside hopper 10. A portion of front wall 14 is removed to accommodate a sonar device 30. Referring also to FIG. 4, sonar device 30 is comprised of generally cylindrical front and back housing sections 32 and 34, respectively. Front housing section 32 is enlarged with respect to back housing section 34. Front housing section 32 includes outer and inner housings 32a and 32b, respectively. Outer housing 32a houses inner housing section 32b, which supports a sonar transducer 36. Transducer 36 is adapted to transmit acoustic energy and receive reflected acoustic energy. A scan axis drive motor 38 is located in inner housing 32b, for selectively rotating transducer 36 about an axis 40, as indicated by rotational arrow 41. Bevel gears 42 and 44 translate the rotational movement of motor shaft 46 approximately 90° to rotate transducer shaft 48 and transducer 36 about axis 40. A protective dome cover 52 is attached to a front end of outer housing 32a for substantially enclosing transducer 36. Transducer 36 and cover 52 define a head portion 53 of sonar device 30.

Head portion 53 is adapted to be immersed in the liquid inside hopper 10, as can be best seen in FIG. 3. Dome cover 52 is capable of withstanding the high water temperature without deformation and is resistant to the corrosive environment inside hopper 10. Dome cover 52 is also capable of withstanding impact from pieces of ash descending through the liquid in hopper 10. Furthermore, because dome cover 52 isolates transducer 36 from the acoustic medium (i.e, the water inside hopper 10), dome cover 52 should be fabricated from a material which is substantially acoustically transparent, so as not to inhibit the transmission of acoustic energy from transducer 36 into the water or the receipt of reflected acoustic energy from the water by transducer 36. After much experimentation it was determined that cover 52 is preferably manufactured from an acrylonitrile butadiene styrene (ABS) thermoplastic material, which provides a desired balance of resistance to corrosion and abrasion, tensile hardness, and temperature and acoustic properties.

Head portion 53 is filled with a liquid material to occupy the space between transducer 36 and dome cover 52. The liquid material transmits the acoustic energy between transducer 36 and cover 52, which transmits the acoustic energy to the water inside hopper 10. Front housing section 32 is preferably made of stainless steel material and transducer 36 is preferably made of aluminum material. Therefore, head portion 53 should not be filled with water because the electrolytic action between the stainless steel and aluminum materials may corrode the transducer components. The liquid material introduced into head portion 53 should therefore have good acoustical transmission properties and low dielectric properties, so that the liquid material provides a favorable medium for the transmission of acoustic energy, but is substantially electrically nonconductive. One such liquid material having the desired properties is Velocite Oil No. 6 spindle oil, manufactured and sold by Mobil Corporation.

Back housing section 34 houses an azimuth axis drive motor 54, which is coupled to inner housing 32b by means of a rotatable shaft 56. Motor 54 is adapted to rotate the inner housing section 32b, and transducer 36 about an axis 58, as indicated by rotational arrow 60. Axis 58 is oriented perpendicular to axis 40 and is coincident with a longitudinal axis of shaft 56.

An annular collar 62 is integrally formed with cover 52 and is in concentric relation about front housing section 32, adjacent head portion 53. Another annular collar 64 is in concentric relation about back housing section 34. An annular mounting member 66 is in concentric relation about front housing section 32, adjacent collar 64, for mounting sonar device 30, as will be described in greater detail hereinafter.

Sonar device 30 is mountable in a fixed position with hopper 10. A generally cylindrical casing 70 having an internal chamber 71 is adapted for insertion into hopper 10. For example, as shown in FIG. 3, a portion of front wall 14 is removed to accommodate casing 70. Casing 70 is adapted to substantially completely enclose all of front housing section 32 in interior chamber 71, except for head portion 53. Casing 70 is preferably made of No. 304 stainless steel material for corrosion protection.

Casing 70 has a generally circular front opening, which is of sufficient diameter to allow head portion 53 to penetrate therethrough into hopper 10. Sonar device 30 is insertable into and retractable from casing 70 through a generally circular back opening 72, which has a larger diameter than the front opening in casing 70. An inner surface 76 of casing 70, which is adjacent the front opening, is adapted to engage a leading surface 62a of collar 62, to limit the penetration of head portion 53 into hopper 10. Casing 70 further includes a locating flange 78, which is adapted to engage an outer surface 62b of collar 62, to inhibit lateral movement of front housing section 32 (i.e., movement along respective radial axes which are perpendicular to a longitudinal axis of front housing section 32). Inner surface 76 and locating flange 78 cooperate with collar 62 to substantially isolate internal chamber 71 from the water in hopper 10.

Casing 70 further includes a mounting flange 80, which projects into chamber 71. A plurality of threaded mounting studs 82 protrude from mounting flange 80 for mating engagement with respective holes (not shown) in mounting member 66 when head portion 53 is immersed in the liquid within hopper 10. A plurality of threaded nuts 84 are adapted to engage the respective studs 82 to secure mounting member 66 to mounting flange 80, whereby sonar device 30 is mounted in a fixed position with respect to casing 70. A gasket 88 is in between mounting member 66 and mounting flange 80. Sonar device 30 is removable from casing 70 by disengaging nut 84 from the respective studs 82 and retracting sonar device 30 from casing 70.

Although internal chamber 71 is isolated from direct contact with the water inside hopper 10, at least some of the heat from the water is transferred into chamber 71. To prevent the build-up of excessive heat in chamber 71, a cooling system is provided. The cooling system includes a source 90 of cooling fluid (preferably water), a valve 92 for controlling the flow of cooling water, a first conduit 94 communicating between source 90 and chamber 71, for supplying cooling water to chamber 71 and a second conduit 96 communicating between chamber 71 and head portion 53, which is immersed in the liquid inside hopper 10, for discharging cooling water from chamber 71 and directing a flow of cooling water on cover 52, to help cool head portion 53. A valve 98 is located in second conduit 96 for controlling the flow of cooling water to cover 52. A check valve 100 prevents the backflow of hot water from inside hopper 10 through second conduit 96.

In operation, cooling water is supplied to chamber 71 through first conduit 94, as indicated by arrows 95, and is discharged from chamber 71 via second conduit 96, as indicated by arrows 97, to maintain a steady flow of cooling water through chamber 71. The flow of cooling water continues through second conduit 96, downstream of valve 98, as indicated by arrows 99, to a discharge opening 102, which communicates with the interior of hopper 10. Outlet 102 is preferably located directly above cover 52 so that the cooling water emanating from outlet 102 is directed on top of and around cover 52, as indicated by arrows 104.

A portion of the refractory material 28 is extended to define a protective hood 106, which deflects descending pieces of solid material away from head portion 53, to prevent cover 52 and the transducer components housed therein from being bombarded by solid material. As shown in FIG. 3, head portion 53 extends a predetermined distance X (e.g., three inches) into hopper 10. Hood 106 preferably extends inwardly a greater distance than X, to effectively shield head portion 53 from the pieces of solid material descending in the water. By reducing the penetration of sonar device 30 into hopper 10, the chances of damage to sonar device 30 by corrosion, excess heat and/or impact from descending material are also reduced, without diminishing the acoustic capability of sonar device 30.

Sonar device 30 is adapted for dual-axis scanning (i.e., scanning along multiple scanning axes at each azimuth position of transducer 36 in a predetermined sequence of azimuth positions). Each scan position of transducer 36 corresponds to a discrete rotational position of transducer 36 with respect to first axis 40. Each azimuth position corresponds to a discrete rotational position of transducer 36 with respect to second axis 58. A standard sonar device, such as the sonar device of the Model 971 type, manufactured and sold by Simrad Mesotech Systems, Ltd. of Port Coquitlam, British Columbia, Canada, is preferably modified to provide the aforementioned dual-axis scanning capability. The dual-axis capability enables sonar device 30 to sample multiple points at each of a plurality of azimuth positions, so that sonar device 30 has a three-dimensional scan capability from a fixed position. Furthermore, the conventional sonar device is also modified to remove the transducer control electronics from the head portion 53 of the sonar device so that the control electronics are not exposed to the hostile environment inside hopper 10.

Figure 5:
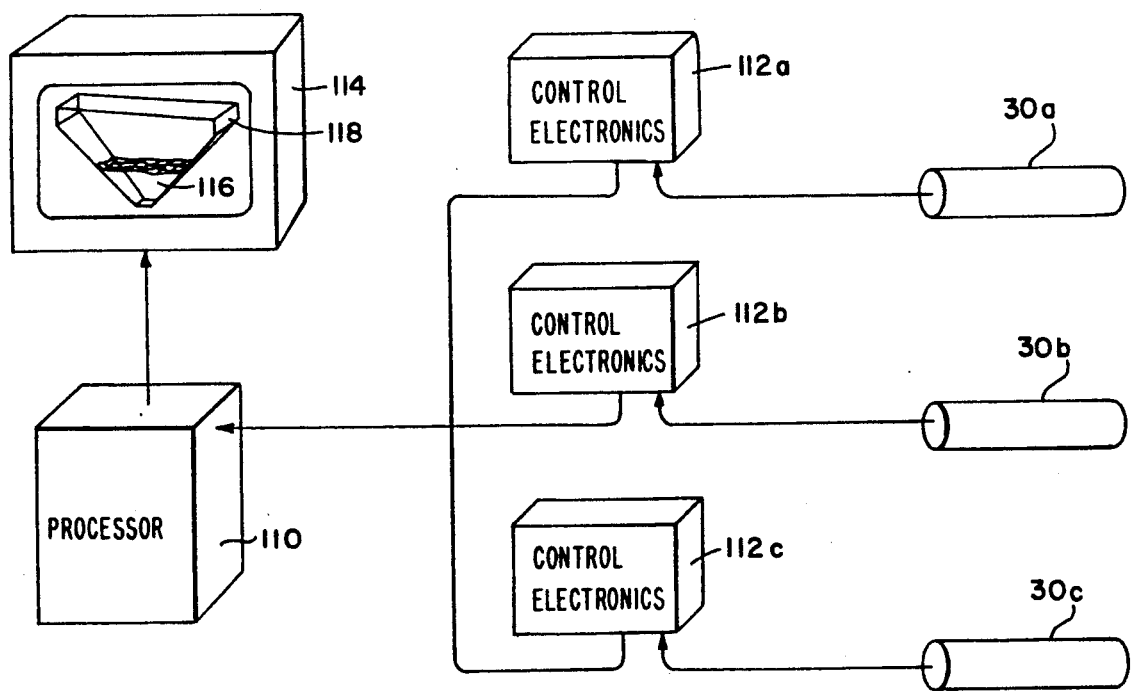
FIG. 5 is a schematic view of a control system for controlling three sonar transducers, according to the present invention.

Referring now to FIG. 5, a processor 110 is used to control the operation of one or more sonar devices. In FIG. 5, three sonar devices 30a, 30b and 30c are controlled by processor 110. Each sonar device 30a, 30b and 30c is mountable with a corresponding separate hopper (not shown). The control electronics 112a, 112b and 112c associated with the respective devices 30a, 30b and 30c are located at a remote location from the respective devices 30a, 30b and 30c, within eight feet of the respective devices 30a, 30b and 30c. Processor 110 receives data from devices 30a, 30b and 30c, via the respective control electronics 112a, 112b and 112c, and controls a video monitor 114 to display a two- dimensional image, which simulates a three-dimensional representation of sediment 116 at the bottom of a hopper 118. Processor 110 is comprised of a plurality of electronic component cards, including a video master card, a telemetry master card and an interface card for communicating with the control electronics 112a, 112b and 112c. Processor 110 is preferably programmed using a plurality of erasable programmable read only memories (EPROM's), to control the sequence of operation of processor 110 and sonar devices 30a, 30b and 30c. The video master card is preferably of the 420-10918800 type, the telemetry master card is preferably of the 420-10811000 type, and the interface card is preferably a MS990 interface card of the 420-12011000 type, all of which are manufactured and sold by Simrad Mesotech Systems, Ltd. as components of its Model 971 sonar device. Processor 110 further includes a VME ten layer backplane board, which is manufactured and sold by, inter alia, Electronic Solutions of San Diego, Calif. The backplane functions as a communications and power supply bus for the various cards in processor 110. A 130 watt switching power supply, with 120 volt AC input and +5, −12 and +12 volt DC output, is also included in processor 110. The power supply is preferably of the type manufactured and sold by, inter alia, Power-One Switching Products of Camarillo, Calif. Video Monitor 114 is preferably a standard VGA 640X480 pixel color monitor, which is commercially available from a variety of suppliers.

Referring now to FIGS. 6–11, the process by which sediment is located in a collection hopper and mapped with reference to the hopper will now be described in detail. The following description will be with reference to a single hopper and a single sonar device. One skilled in the art will recognize that the process is equally applicable to multiple unit hopper sections and multiple sonar devices.

Figure 6:
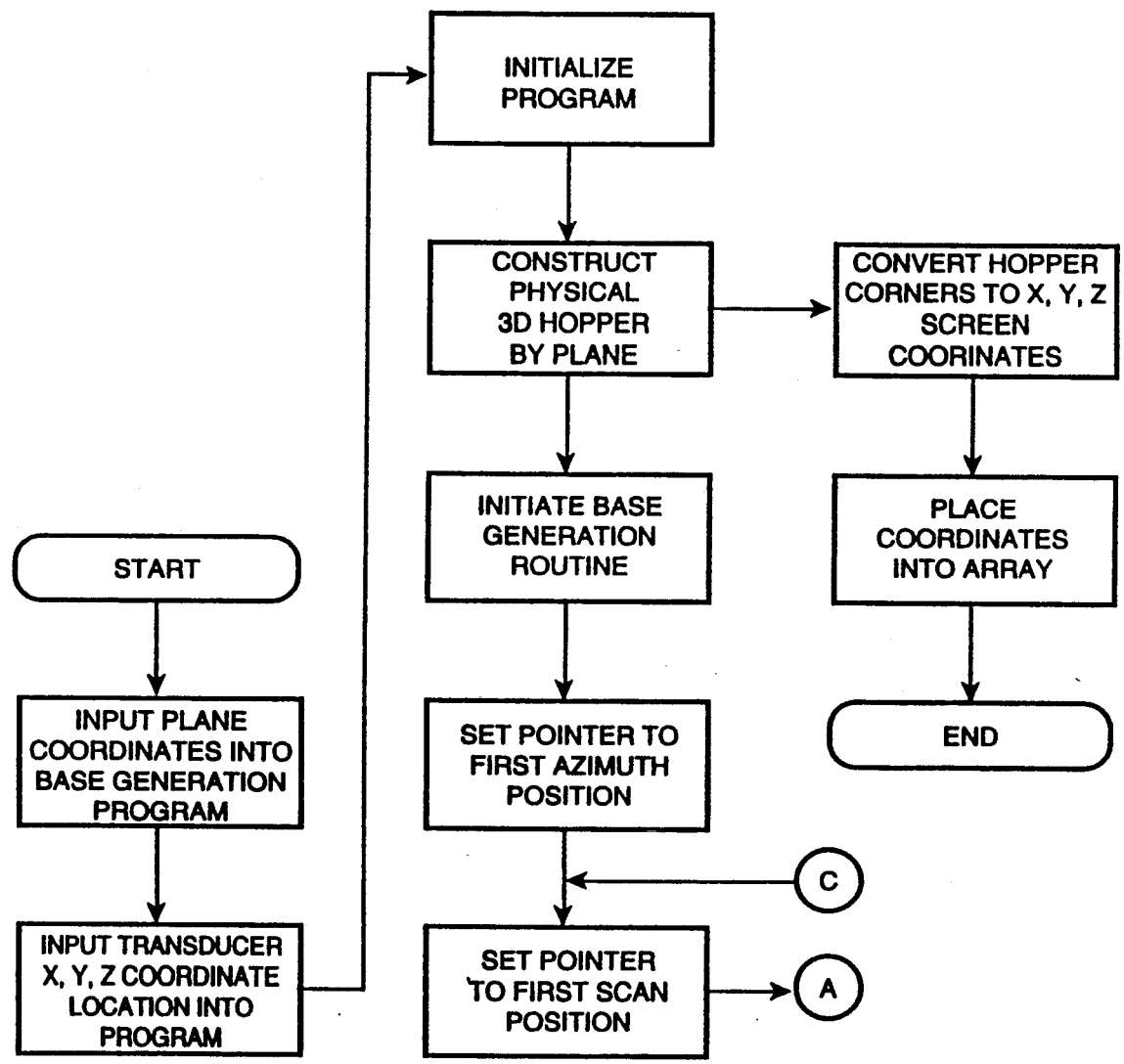
FIGS. 6–11 are respective flow diagrams, illustrating the process by which sediment in a collection hopper is located and mapped, the present invention.
Figure 7:
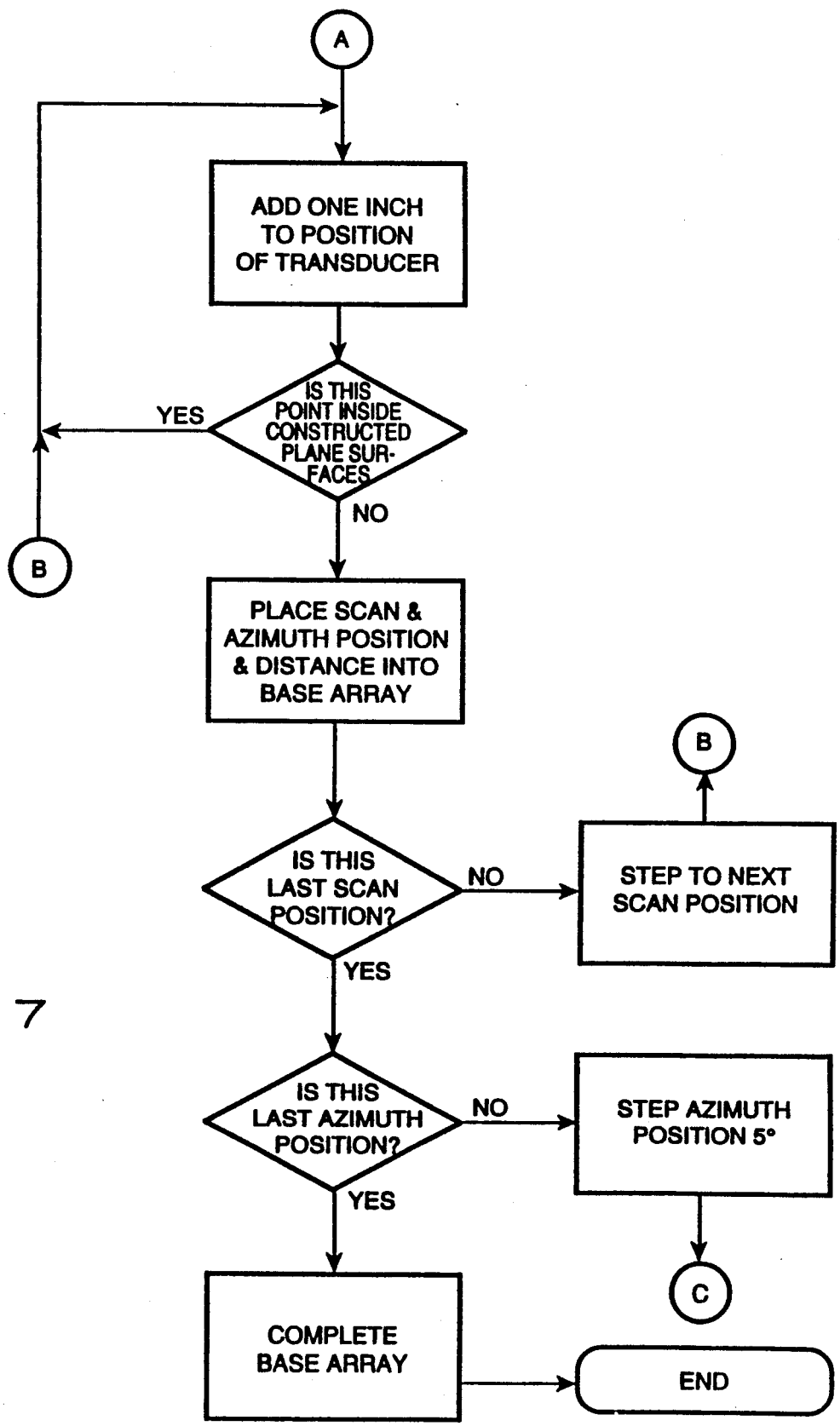

Referring specifically to FIGS. 6 and 7, a routine is depicted for creating a reference database corresponding to the configuration of an empty hopper. Referring also to FIG. 12, the operator constructs a three-dimensional Cartesian coordinate system (x, y, z coordinates) and assigns discrete position coordinates to each corner point of hopper 10. One of the corner points 120 is assigned as a point of origin (0, 0, 0) in the Cartesian coordinate system. All of the other corner points are assigned corresponding x, y, z space coordinates, with reference to the origin point. The operator organizes the three-dimensional hopper 10 into a plurality of interconnecting geometric planes. The operator then inputs the respective coordinates of the corner points of each plane and the coordinates of transducer 36, which is mounted on front wall 14 of hopper 10 in FIG. 13, into the processor. After the coordinates of each corner point have been entered into the processor, the processor initializes a base generation routine (FIG. 6) to construct the three-dimensional hopper based on the input coordinates of the corner points of each plane. The processor converts the input coordinates to three-dimensional screen coordinates and connects the corner points of each plane to construct a three-dimensional "wire frame" of hopper 10 in an empty condition. The screen coordinates of each corner point represent corresponding pixel locations and are stored in a data array.

Referring now to FIG. 7, the respective distances from the sonar transducer 36 to selected points on an inner surface of hopper 10, are determined to create a reference database. The processor sets a pointer to a first azimuth position in a predetermined sequence of azimuth positions. Each azimuth position corresponds to a discrete rotational position of the transducer 36 about a longitudinal axis of sonar device 30, which corresponds to axis 58 in FIG. 4. For example, the processor may be programmed to control motor 54 to rotate transducer 36 about axis 58 in predetermined angular increments (e.g., 5° or 10°) of a predetermined angular interval (e.g., from −70° to +70°). If the first azimuth position corresponds to −70°, the pointer is set initially to that position. In FIG. 12, sonar device 30 is mounted on front wall 14 of hopper 10, such that the longitudinal axis of sonar device 30 extends horizontally toward back wall 16. Axis 58 is therefore oriented along a horizontal axis between front and back walls 14 and 16. In this orientation, the rotation of transducer 36 about axis 58 actually rotates transducer 36 about the longitudinal axis of sonar device 30. The 0° azimuth position therefore corresponds to a downwardly directed vertical axis, which is perpendicular to horizontal axis 58. For purposes of explanation, it will be assumed that the first azimuth position corresponds to the −70° azimuth position, as can be best seen in FIG. 14, although the operator can program any other azimuth position as the first azimuth position. The operator can also select the angular increments between azimuth positions (either 5° or 10° increments).

The scan pointer is also set to the first scan position. As can be best seen in FIGS. 12 and 13, each scan position corresponds to a discrete scanning axis, represented by each arrow 122 emanating from transducer 36 in FIG. 14. Although any of the scan lines can be selected as the first scan position, for purposes of explanation, it will be assumed that the first scan position corresponds to a horizontal scan axis 122a, which also coincides with longitudinal axis 58.

Referring again to FIG. 7, the processor will then determine the distance from transducer 36 to a point on an inner surface of hopper 10 along the first scan line 122a, at the first azimuth position. The distance along first scan line 122a to the inner surface of hopper 10 is determined by iteratively adding one inch increments to the position of transducer 36 until the position of transducer 36 is no longer inside a plane surface representing a corresponding inner surface of the hopper. The determined distance is stored as a reference distance, along with the corresponding scan position and azimuth position, in the base array. The reference distance represents the distance between transducer 36 and a discrete position 124a on an inner surface of the hopper along the first scan axis 122a.

The reference distance is obtained along each scan axis 122 in sequence until the respective reference distances have been obtained for all of the scan axes 122 in a first discrete group of scanning axes. As previously mentioned, the first scan axis 122a preferably corresponds to horizontal axis 58, while the last scan axis 122b is perpendicular to horizontal axis 58, such that transducer 36 is programmed to scan through a 90° angular interval. Point 124b corresponds to a position on an inner surface of hopper 10 along the last scan axis 122b. In the preferred embodiment, each scan axis is separated from an adjacent scan axis by an angular increment of approximately 0.225°, such that the 90° angular interval will include 400 discrete scanning axes 122. After the respective reference distances along all of the scanning axes 122 are obtained at the first azimuth position, transducer 36 is rotated about horizontal axis 58 to the next azimuth position in sequence and the respective reference distances along a second discrete group of scanning axes are obtained for the next azimuth position in sequence. The process is iteratively performed until the respective reference distances are obtained for all the scanning axes 122 at each of the azimuth positions. If consecutive azimuth positions are set 5° apart there will be 29 discrete azimuth positions, beginning at −70° and ending at +70° (i.e., a 140° azimuth interval).

As can be best seen in FIG. 14, the respective reference distances along the respective scanning axes at each azimuth position can be represented as a series of discrete points 124, representing discrete positions along an inner surface of hopper 10. The points 124 can be connected to define a discrete two-dimensional profile at each azimuth position. FIG. 14 illustrates the two-dimensional profiles corresponding to azimuth positions −70°, −45°, 0°, +45° and +70°. Although only five two-dimensional profiles are shown in FIG. 14, one skilled in the art will recognize that discrete two-dimensional profiles are obtained at each azimuth position. Each two-dimensional profile is oriented in a different plane from the other profiles. The profile at the 0° azimuth position is oriented in a vertical plane. FIG. 14 also illustrates that when the first scanning axis 122a corresponds to the longitudinal axis 58, the first scanning axis 122a and the first point of reflection 124a are the same at each of the azimuth positions. The location and the reference distance corresponding to each point 124 comprise a discrete base array data entry for the corresponding point 124. The data entries for all of the points 124 comprise the base array.

Figure 8:
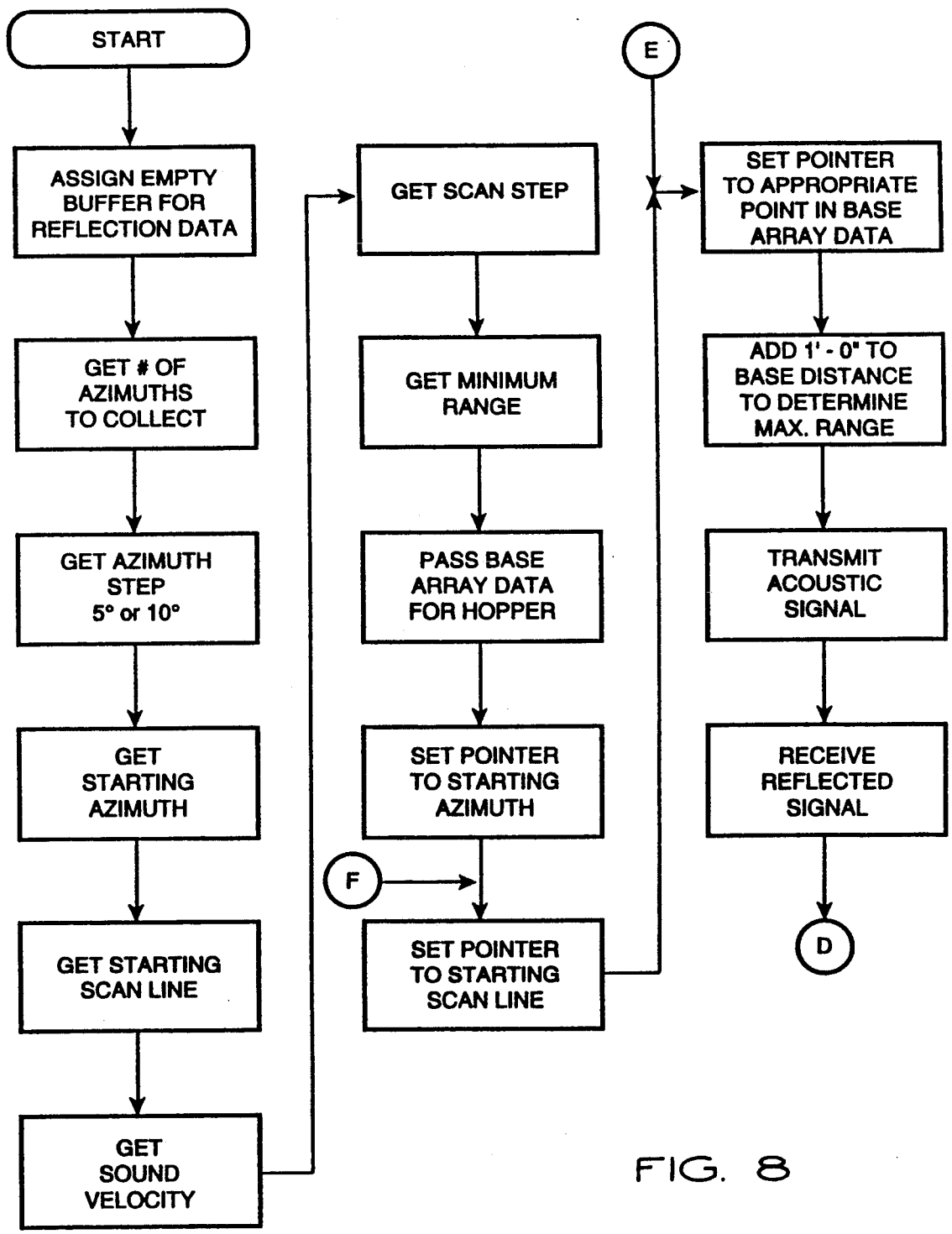

Referring now to FIG. 8, a control routine is initialized for controlling the transducer to emit discrete acoustic signals into the hopper and to receive reflected acoustic signals, so that the location of the sediment within the hopper can be determined. Upon initialization, an empty buffer is assigned for storing data relating to the reflected acoustic signals. The processor is responsive to operator input commands for determining the number of azimuth positions to be sampled, the azimuth step (i.e., 5° or 10°) and the starting azimuth position. In the absence of operator input commands, the default number of azimuth positions is 15, the default azimuth step is 10° and the default azimuth starting position is −70°.

The processor then determines the starting scan axis, the sound velocity parameter, the scan step and the minimum distance parameter, in response to operator input commands. The default starting scan axis corresponds to horizontal axis 58, the default scan step is one (i.e., every scan axis) and the default minimum range is two feet. The default sound velocity is 4,800 feet per second. Sound velocity is used to determine the distance between the transducer and a point of reflection along a corresponding scan line.

The operator is able to control the sound velocity parameter used by the processor in computing distance data. If the sound velocity parameter used to compute the distance parameters is below the actual sound velocity, the walls of the hopper 10 will appear inside of the corresponding walls of the "wire frame" image of the hopper 10. This condition is remedied by increasing the sound velocity parameter until the walls of the hopper coincide with the "wire frame" image of the hopper 10. By the same token, if the sound velocity parameter is set too high, the walls of the hopper 10 will appear outside the "wire frame" image of the hopper 10. In this condition some of the sediment which is actually in the container will not appear in the resulting image.

The base array data, which includes the predetermined reference distance parameters for the empty hopper, is stored in an appropriate memory location. The azimuth pointer is then set to the starting azimuth position and the scan point is set to the starting scan axis. A reference pointer is also set to the appropriate position in the base array data, which corresponds to the starting scan axis and the starting azimuth position. The processor then adds one foot to the corresponding reference distance so that any reflected acoustic signal which indicates a distance more than one foot greater than the predetermined reference distance is ignored, to eliminate multiple reflected signals. The processor sends a control signal to the control electronics, which activates the transducer to transmit a discrete acoustic signal along the starting scan axis at the starting azimuth position and to receive the reflected acoustic signal.

Figure 9:
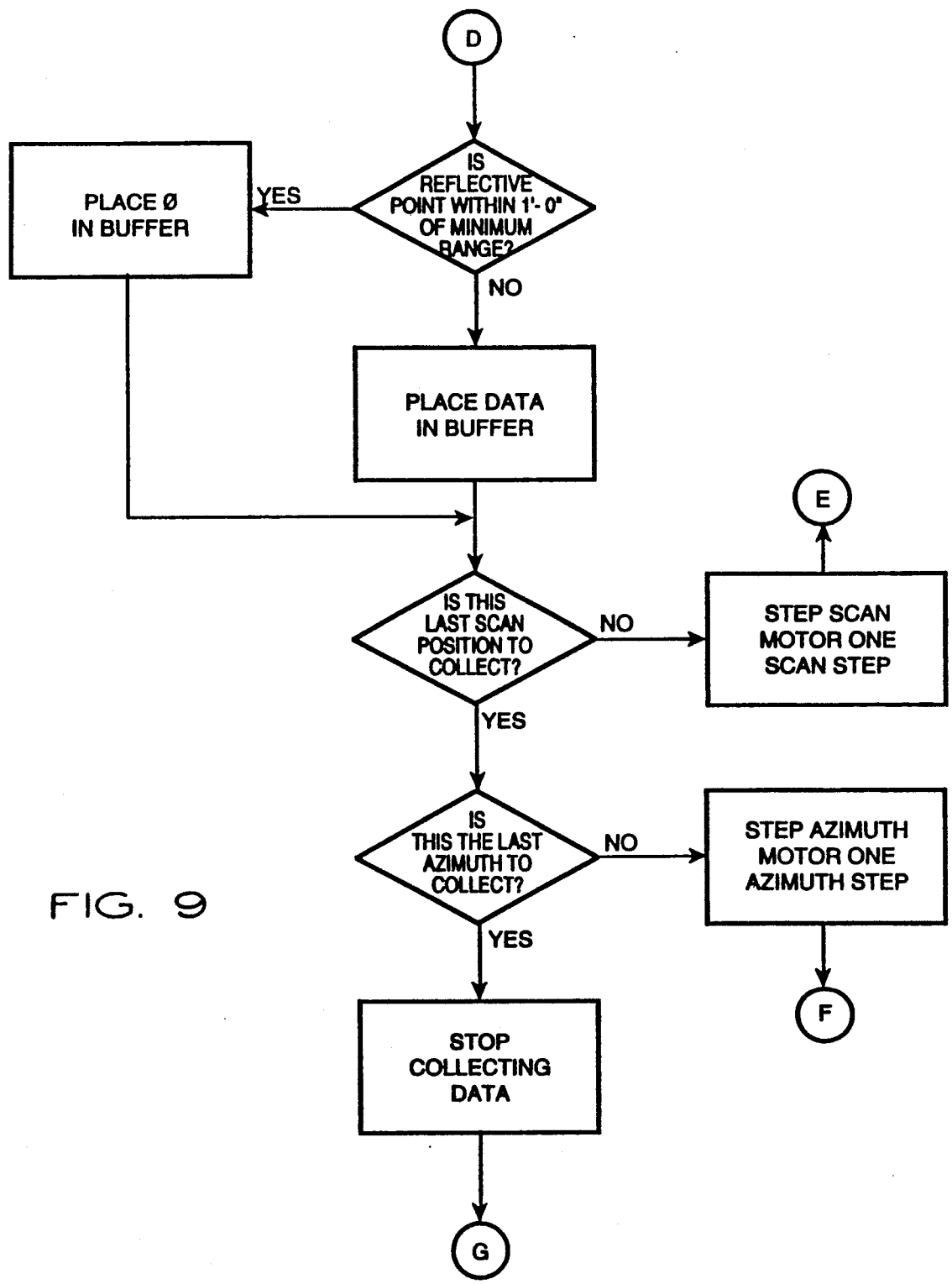

Referring now to FIG. 9, if the reflected acoustic signal indicates that the distance between the transducer and the point of reflection is within one foot of the preselected minimum distance parameter, a "0" entry will be placed at the appropriate position in the data buffer. If the distance is not within one foot of the minimum distance parameter, the distance data for the first scan axis at the first azimuth position will be placed at the appropriate location in the buffer. The distance data represents the distance between the transducer and a point of reflection along the first scan axis at the first azimuth position.

Figure 15:
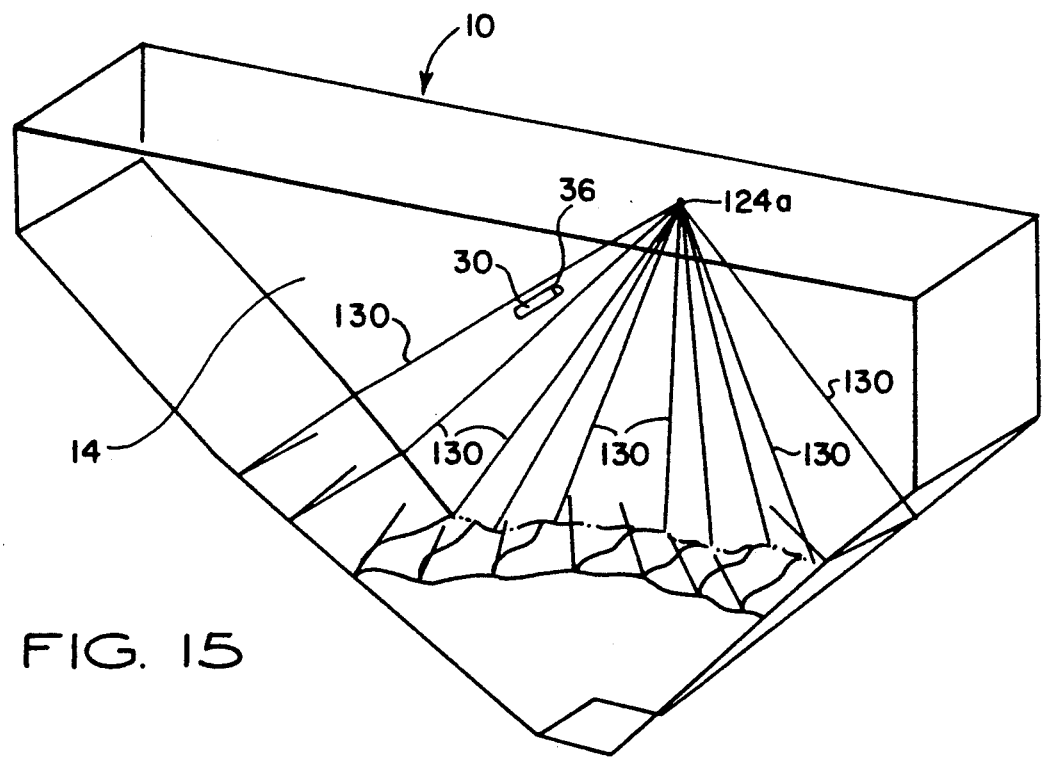
FIG. 15 is a perspective view of a collection hopper, illustrating discrete two-dimensional profiles of points of reflection in a collection hopper, with sediment present in the hopper.

The aforementioned procedure is iteratively performed in sequence for each of the scan lines in the aforementioned first group of lines. When the respective distances have been measured along all of the scan lines in the first group, the transducer is moved to the next azimuth position and the process is iteratively performed with respect to all of the scan lines in the aforementioned second group of scan lines. The process is iteratively performed until all of the selected scan axes have been sampled at each of the selected azimuth positions. The result is a plurality of two-dimensional profiles 130, as shown in FIG. 15. Each profile 130 is comprised of sequential points of reflection along the respective scan axes at a corresponding azimuth position.

Figure 10:
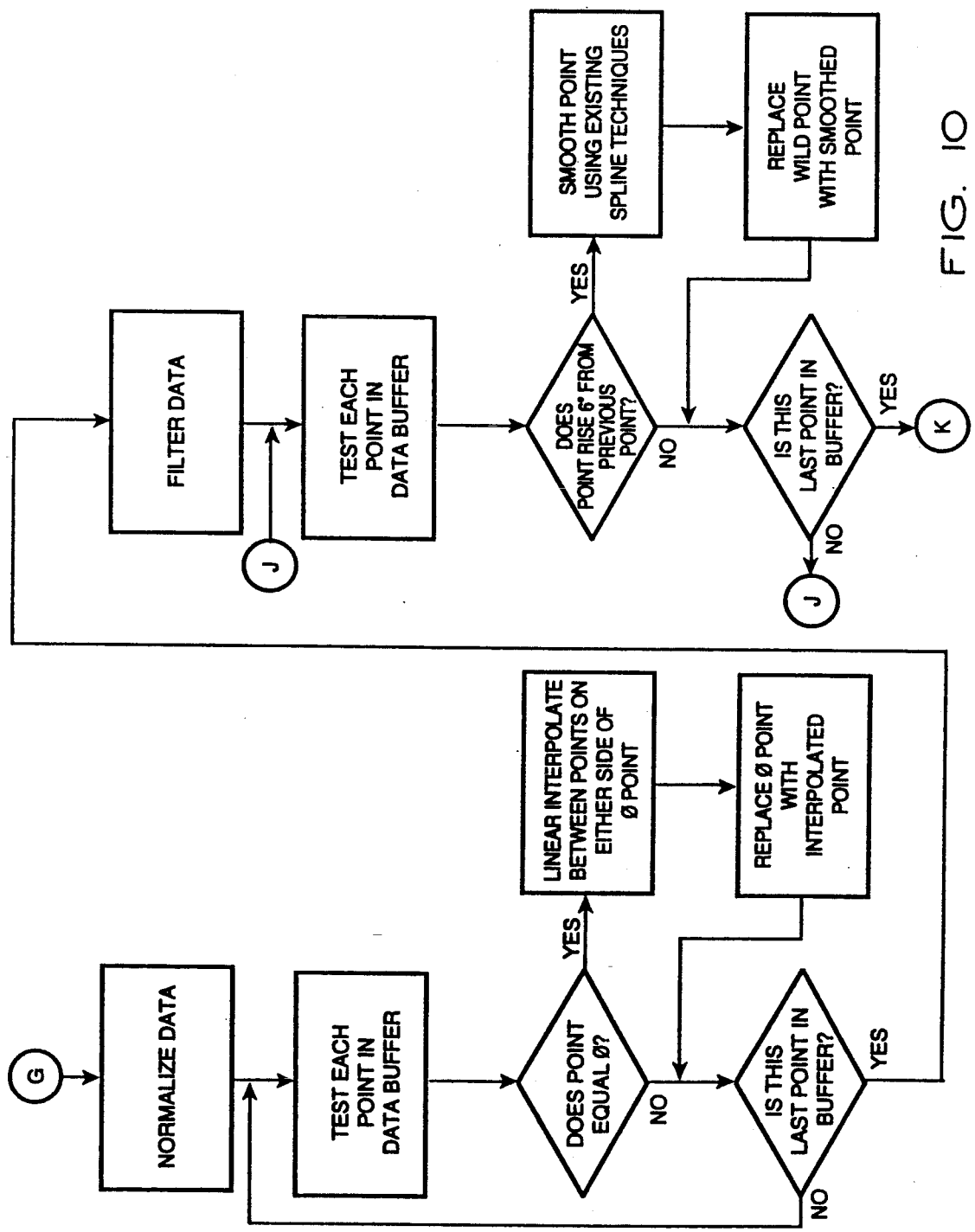

Referring now to FIG. 10, the distance data is normalized and each of the data entries is tested. If a data entry indicates "0" (i.e., the distance is within one foot of the preselected minimum distance or no reflected signal is detected), the processor linearly interpolates between points on either side of the zero point and replaces the zero point with an interpolated distance. The aforementioned process is iteratively performed for all of the data entries.

After the distance data has been normalized and tested, the data is filtered and tested further. Even if a data entry does not indicate "0", the data entry for each point is compared with the data entry for a previous point to determine if an aberration exists. For example, solid material which is descending through the liquid in the hopper, but has not yet come to rest as sediment, may reflect an acoustic signal, which will result in an invalid data entry. Therefore, the processor compares the distance data for each point with the corresponding distance data of a previous point in the corresponding profile. If the distance data indicates that the point is six inches or more closer to the transducer than the previous point, it is assumed that the point corresponds to a piece of material which is still suspended in the liquid. The distance data for that particular point is discarded and conventional spline techniques are used to replace the discarded distance data with a "smoothed" data entry. The aberration or "wild point" is therefore replaced with the "smoothed" point, using conventional spline techniques. The aforementioned filtering process is iteratively performed for each point in the buffer until all of the points have been filtered.

Figure 11:
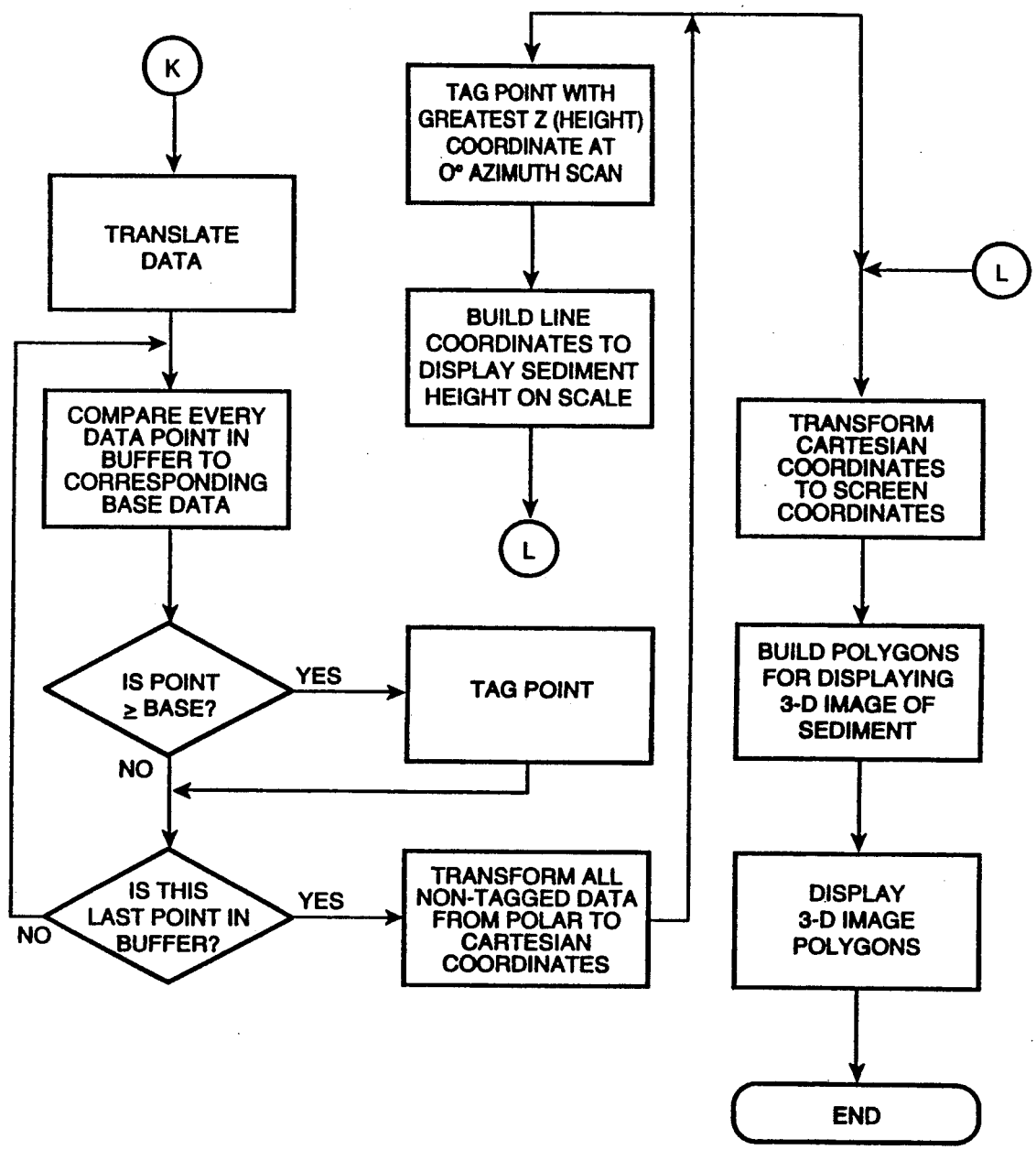

Referring now to FIG. 11, a data translation routine is initiated, whereby the distance data for every point in the buffer is compared to the corresponding reference distance. If the distance data corresponding to a particular point indicates that particular point is at the same or greater distance than the corresponding reference distance, the point will be "tagged". The translation routine is iteratively performed for every point in the buffer.

Figure 16:
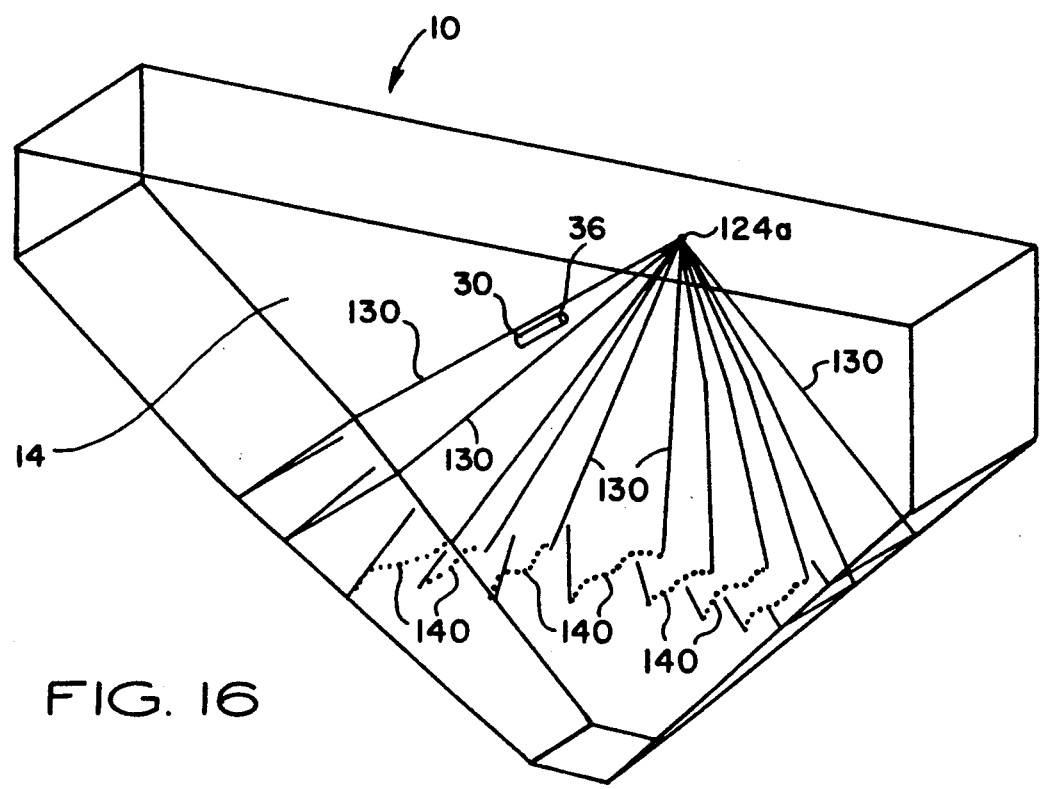
FIG. 16 is a perspective view of a collection hopper, illustrating the discrete two-dimensional profiles of FIG. 15, wherein points of reflection on the sediment in the hopper are distinguished from points of reflection on corresponding inner surfaces of the hopper.
Figure 17:
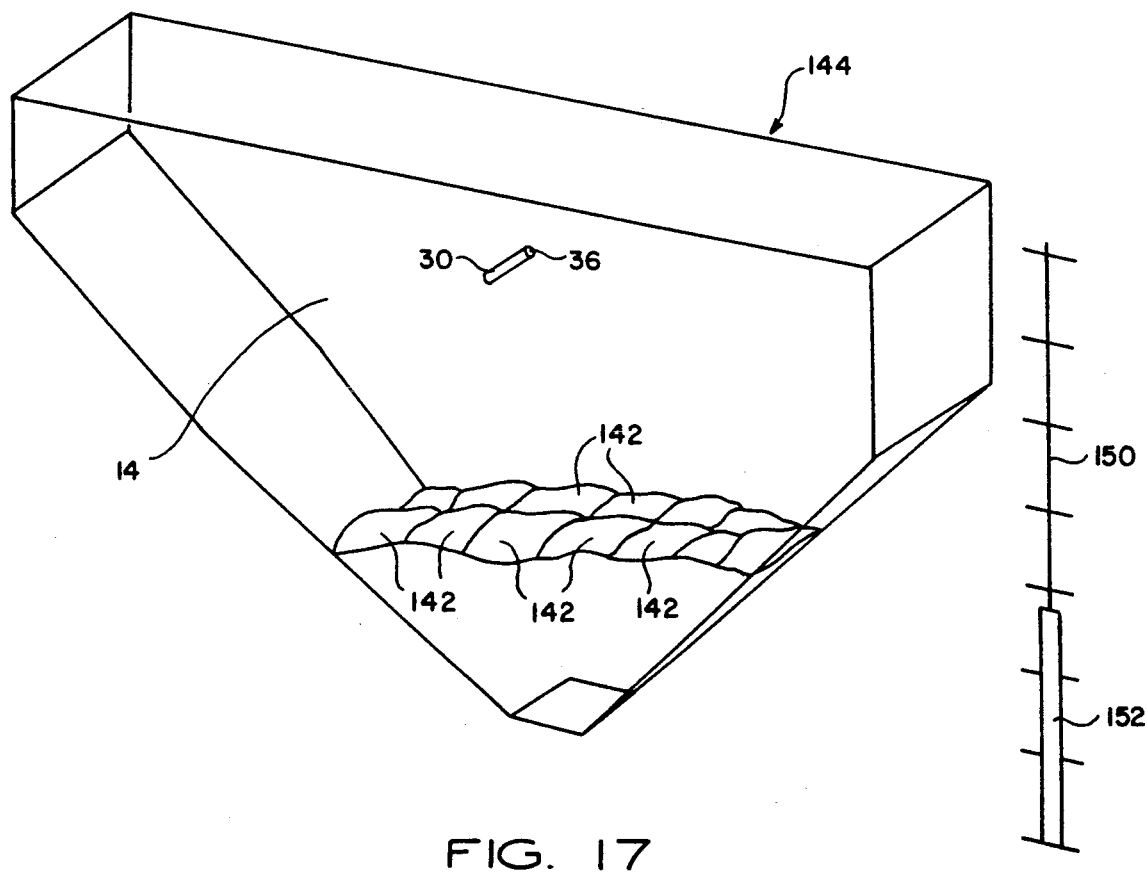
FIG. 17 is a perspective view, illustrating a three-dimensional representation of the sediment in a collection hopper, superimposed on a three-dimensional representation of the hopper.

At the conclusion of the translation routine, all of the points are identifiable as being either "tagged" or "non-tagged". The non-tagged points corresponding to respective locations on a top layer of sediment in hopper 10, as indicated by points 140 in FIG. 16. The non-tagged points 140 are represented by the dots in FIG. 16. The tagged points are indicated by the solid lines in FIG. 16, which correspond to the hopper surfaces. Heretofore, the position of each point has been indicated with reference to a three-dimensional polar coordinate system. The processor transforms all of the respective polar coordinates of the non-tagged points to corresponding Cartesian coordinates. The Cartesian coordinates are then transformed to corresponding screen coordinates for visual display. The screen coordinates and distance data corresponding to each non-tagged point are used to build a series of polygons 142 for displaying a three-dimensional image of sediment at the bottom of hopper 10, as shown in FIG. 17. The three-dimensional image of the sediment is superimposed on a three-dimensional "wire frame" image 144 of the empty hopper, so that one can visually determine the amount and location of the sediment in the hopper.

One skilled in the art will recognize that the "non-tagged" points are those points which are at a lesser distance from the transducer than the corresponding reference distance along the same scan axis. The lesser distance indicates that sediment has been deposited between the wall of the hopper and the transducer, along the corresponding scan axis. By determining the coordinates of the each of the non-tagged points, with reference to the origin point, a three-dimensional map of the sediment is obtained and displayed on a two-dimensional screen. By super imposing the three-dimensional image of the sediment on the "wire frame" image 144 of the hopper, one can visually determine the amount and location of the sediment in the hopper.

The processor can also determine the highest level of the sediment in the hopper by determining the highest point at the 0° azimuth position. The highest point corresponds to the "non-tagged" point which is determined to be the closest to the transducer, at the 0° azimuth position. The 0° azimuth position is shown in FIG. 14 and corresponds to an azimuth position at which the resulting two-dimensional profile of the corresponding reflection points 124 lies in a vertical plane.

Referring again to FIG. 17, a scale 150 is provided to indicate the highest level of sediment in the hopper. A vertical bar 152 is overlaid on scale 150 to indicate the highest level sediment.

The present invention provides a dynamic three-dimensional image of sediment in a collection hopper. The sediment is located and mapped in accordance with a unique feature of the invention, whereby the sediment is detected with directional acoustic signals and distinguished from the walls of the hopper by comparing the respective distances between the source of the acoustic signals and respective points of reflection to respective reference distances representing the respective distances between the source of the acoustic signals and an inner surface of the hopper. The presence of sediment is indicated when the distance to a reflective point is less than the predetermined distance to an inner surface of the hopper along a corresponding direction. In accordance with the present invention, the sediment can be removed as needed, rather than according to an arbitrary time schedule.

Various embodiments of the invention have now been described in detail. Since it is obvious that many changes in and additions to the above-described preferred embodiment may be made without departing from the nature, spirit and scope of the invention, the invention is not to be limited to said details, except as set forth in the appended claims.

What is claimed is:

1. Apparatus for locating sediment in a container, which is at least partially filled with liquid, said apparatus, comprising, in combination:

transducer means mountable with said container for emitting acoustic energy into the liquid and for receiving reflected acoustic energy, said transducer means being rotatable about first and second mutually perpendicular axes;

rotational means for rotating said transducer means about mutually perpendicular first and second axes;

control means for controlling said rotational means to rotate said transducer means about the respective first and second axes and for controlling said transducer means to emit an acoustic signal into the liquid and receive a corresponding reflected acoustic signal at each rotational position of said transducer means in a predetermined sequence of rotational positions, each rotational position being definable by a first rotational coordinate with respect to said first axis and a second rotational coordinate with respect to said second axis;

processing means responsive to the reflected acoustic signals for determining respective distances between said transducer means and respective points of reflection along respective scanning axes corresponding to the respective rotational positions of said transducer means and for comparing the computed distance at each scanning axis with a predetermined reference distance representing the distance between the transducer means and an inner surface of the container along the corresponding scanning axis, said processing means including means for identifying each point of reflection whose distance to the transducer means is less than the corresponding reference distance, the identified points of reflection representing respective locations of sediment in the container; and image processing means for processing the identified points of reflection to provide a three-dimensional representation of the sediment in the container.

2. The apparatus of claim 1 further including mounting means for mounting said transducer means with said container, said mounting means comprising, in combination:

a casing adapted for insertion into the container, said casing having an internal chamber for receiving said transducer means and an opening communicating between said internal chamber and the liquid in the container when the casing is inserted into the container; and a mounting flange projecting from said casing into said chamber for mounting for said transducer means in a fixed position with respect to said casing such that a first portion of said transducer means is able to penetrate through said opening into the liquid and a second portion of said transducer means is carried in said chamber.

3. The apparatus of claim 2 wherein said transducer means includes a housing and a collar member in concentric relation about said housing, said collar member being adapted to contact an inner surface of said casing adjacent said opening for substantially isolating said chamber from said liquid.

4. The apparatus of claim 3 wherein said casing further includes a locating flange projecting into said chamber adjacent said opening for engaging an outer surface of said collar member when said collar member is in said contact with said inner surface, said locating flange cooperating with said inner surface to substantially isolate said chamber from the liquid, said locating flange being adapted to limit movement of said housing in a direction perpendicular to a direction in which said first portion is moveable through said opening into the liquid.

5. The apparatus of claim 2 further including fluid supply means for supplying cooling fluid to cool said transducer means, said fluid supply means including a first conduit for supplying fluid to said chamber, a second conduit for discharging cooling fluid from the chamber and a third conduit for directing a flow of cooling fluid on said first portion of said transducer means when said first portion is in contact with the liquid in the container.

6. The apparatus of claim 2 further including fluid supply means for supplying cooling fluid to said chamber and fluid discharge means for discharging the cooling fluid from said chamber, whereby said transducer means is cooled.

7. The apparatus of claim 2 further including deflector means located in said container above said opening for deflecting solid material descending in said liquid away from said first portion when said first portion is in contact with the liquid in the container.

8. The apparatus of claim 2 wherein said transducer means includes a housing and a mounting collar in concentric relation about the housing, said mounting collar being adapted for attachment to said mounting flange, whereby said transducer means is mountable in said fixed position.

9. The apparatus of claim 1 wherein said transducer means includes:
   a substantially enclosed housing adapted to be immersed in said liquid;
   acoustic signal generating means located in said housing for emitting said acoustic signals;
   acoustic signal receiving means located in said housing for receiving said reflected acoustic signals, said housing being adapted to substantially isolate said acoustic signal generating means and said acoustic receiving means from said liquid; and
   fluid material located in said housing for enhancing the transmission of acoustic energy between said acoustic signal generating means and said housing and between said acoustic signal receiving means and said housing.

10. The apparatus of claim 9 wherein said fluid material is substantially electrically non-conductive.

11. A method of locating sediment in a container, which is at least partially filled with liquid, said method comprising the steps of:
   providing transducer means for emitting acoustic energy and for receiving reflected acoustic energy, said transducer means being rotatable about first and second mutually perpendicular axes;
   mounting the transducer means with the container so that the transducer means is adapted to emit acoustic energy into the liquid and to receive reflected acoustic energy;
   positioning said transducer means at a first rotational position with respect to said first axis in a predetermined sequence of discrete rotational positions by rotating said transducer means about said first axis;
   rotating said transducer means in predetermined rotational steps about said second axis and controlling said transducer means to emit a discrete acoustic signal into the liquid and to receive a corresponding reflected acoustic signal along a corresponding scanning axis at each rotational step;
   computing the distance between the transducer means and a corresponding point of reflection along each scanning axis in response to the corresponding reflected acoustic signal;
   comparing the computed distance along each scanning axis with a corresponding predetermined reference distance representing the distance between the transducer means and an inner surface of the container along the corresponding scanning axis;
   identifying each point of reflection whose computed distance is less than the corresponding reference distance;
   creating a two-dimensional profile of the identified points of reflection, said profile representing respective locations of sediment in the container;
   sequentially repeating said rotating, said controlling, said computing, said comparing, said identifying and said creating at each rotational position in said predetermined sequence, to generate a discrete two-dimensional profile corresponding to each rotational position in said predetermined sequence; and
   combining said plurality of two-dimensional profiles to provide a three-dimensional image of the sediment in the container.

12. The method of claim 11 further including the steps of providing a three-dimensional image of the container in an empty condition and superimposing the three-dimensional image of the sediment on the three-dimensional image of the container, whereby the quantity and location of the sediment in the container are visually determinable.

13. The method claim 11 further including computing the reference distance along each scanning axis before said positioning by the following steps:
   establishing a three-dimensional coordinate system and assigning respective three-dimensional coordinates to respective corner points of the container;
   using the respective coordinates of the corner points to represent the container as a plurality of geometric planes;
   determining the respective distances from the transducer means to an inner surface of the container along the respective scanning axes at each rotational position of the transducer means; and
   storing the determined distances as the respective reference distances.

14. The method of claim 11 further including establishing minimum and maximum distance parameters, comparing each computed distance with the minimum and maximum distance parameters and eliminating points of reflection from the corresponding profile which are less than the minimum distance parameter or greater than the maximum distance parameter.

15. The method of claim 11 further including comparing the computed distance to a point of reflection along each scanning axis with the computed distance to a point of reflection along a previous scanning axis in a corresponding profile and eliminating the corresponding point of reflection from the corresponding profile if the computed distance to the corresponding point of reflection is less than the computed distance to the previous point of reflection by more than a predetermined amount.

16. The method of claim 15 further including replacing each eliminated point of reflection with a replacement point of reflection by interpolating between the previous point of reflection and a next successive point of reflection in the corresponding profile.

17. The method of claim 11 further including determining a maximum level of the sediment in the container by determining a closest distance from the transducer means to an identified point of reflection in a profile of identified points of reflection which is oriented in a vertical plane, said closest distance indicating the maximum level of sediment in the container.

18. The method of claim 17 further including providing indicator means external to the container for visually indicating the determined maximum level of sediment in the container.

* * * * *